United States Patent [19]

Ouchi et al.

[11] Patent Number: 4,690,175

[45] Date of Patent: Sep. 1, 1987

[54] FLEXIBLE TUBE FOR ENDOSCOPE

[75] Inventors: Teruo Ouchi, Saitama; Hiromichi Shibuya, Tokyo, both of Japan

[73] Assignee: Kabushiki Kaisha Medos Kenkyusho, Tokyo, Japan

[21] Appl. No.: 806,379

[22] Filed: Dec. 9, 1985

Related U.S. Application Data

[60] Continuation-in-part of Ser. No. 512,376, Jul. 11, 1983, abandoned, which is a division of Ser. No. 441,998, Nov. 16, 1982, Pat. No. 4,495,134.

[51] Int. Cl.$^4$ ................................................ A61B 1/06
[52] U.S. Cl. ........................................ 138/131; 128/4; 604/282
[58] Field of Search ............... 138/131, 130, 125, 132, 138/144, 129; 128/4; 264/512, 516, 248; 604/282, 280

[56] References Cited

U.S. PATENT DOCUMENTS

| | | | |
|---|---|---|---|
| 2,269,823 | 1/1942 | Kreiselman | 604/280 |
| 2,472,483 | 6/1949 | Krippendorf | 604/282 |
| 2,691,900 | 10/1954 | Brickmar | 138/131 |
| 2,706,494 | 4/1955 | Morse | 138/131 |
| 3,416,531 | 12/1968 | Edwards | 604/282 |
| 3,755,032 | 8/1973 | Higbee | 138/125 |
| 3,924,632 | 12/1975 | Cook | 604/282 |
| 3,944,453 | 3/1976 | Chudgar et al. | 138/132 |
| 3,948,251 | 4/1976 | Hosono | 128/4 |
| 3,997,386 | 12/1976 | Oshida et al. | 264/248 |
| 4,329,980 | 5/1982 | Terada | 128/4 |
| 4,516,972 | 5/1985 | Samson | 138/130 |

Primary Examiner—Stephen Marcus
Assistant Examiner—Leo J. Peters
Attorney, Agent, or Firm—Steinberg & Raskin

[57] ABSTRACT

A flexible tube for use in an endoscope comprises a flexible basic tubular core structure including an outer meshwork tube, and a thermoplastic synthetic resin tube bonded to the outer meshwork tube of the tubular core structure in a manner such that the resin tube maintains an inherent compressive pre-stress in the finished flexible tube. An endoscope tube having flexibility which varies in a step-wise manner from one end of the tube to the other is obtained by integrally bonding two or more thermoplastic synthetic resin tube sections formed of respective resin materials having different hardnesses to the outer surface of the tubular core structure to form a coating layer in an analogous manner. The ends of adjacent tube sections substantially abut each other and upon heating the tube sections to a temperature only slightly higher than a softening point but lower than a melting point of any one of them, the localized regions of the respective pairs of abutting tube section ends are heated to a temperature which is as close as possible to a melting point of one of the tube sections having a higher melting point than that of the other tube section, whereby the end of the other tube section having a lower melting point is fused with the end of the adjacent tube section, and after cooling of the tube sections, a continuous and integral tube is obtained without any joints or junctures.

3 Claims, 7 Drawing Figures

FLEXIBLE TUBE FOR ENDOSCOPE

BACKGROUND OF THE INVENTION

This is a continuation-in-part of application Ser. No. 512,376 filed July 11, 1983 now abandoned which is a divisional of application Ser. No. 441,998 filed Nov. 16, 1982, now U.S. Pat. No. 4,495,134.

The present invention relates generally to flexible tubes for endoscopes and, more particularly, to new and improved tubes for endoscopes having improved flexibility, torsional rigidity and resistance to compression for facilitating insertion of the tube into the body cavity.

Generally, conventional flexible tubes for endoscopes are formed of a basic tubular core structure including a metallic tubular spiral, sometimes referred to as FLEX, whose outer surface is covered by a meshwork tube, the outer surface of the tubular core structure itself being covered in one of two ways. In a first construction, a pre-molded synthetic resin tube is applied over the basic tubular core structure to cover the same while in a second typical construction, a thermoplastic elastic body is directly molded around the tubular core structure to cover the same.

In the flexible tube of the first type described above, the basic tubular core structure is not adhered to the pre-molded synthetic resin tube and, consequently, wrinkles are often formed in the outer surface of the flexible tube as the latter is guided around a curved path during the introduction of the flexible tube into the body cavity. Another problem is that the flexible tube is not sufficiently rigid in compression to be able to resist the compressive forces on the tube caused during the introduction thereof into the body cavity. Moreover, the well known flexible tubes of this type have also lacked good torsional rigidity, i.e., have poor rotation-following characteristics, so that twists are often formed in the flexible tube by ordinary rotary manipulation thereof. Such twists, once formed, frequently cause the flexible tube to become caught between inner walls or folds of the body cavity. For these reasons, the introduction of such conventional flexible endoscope tubes is often painful to the patient and it is not always possible to achieve a smooth introduction in any event. Furthermore, twists formed in the flexible tube can prevent the physician operating the endoscope from observing a desired region or object at a certain location through the forward end of the flexible tube.

In the conventional flexible tube construction of the latter type described above, some thermoplastic elastic material often protrudes randomly through gaps present in the basic tubular core structure during the molding procedure and bonds onto the inner surface of the flexible tube thereby causing the inner surface of the flexible tube to be uneven. As a result, it has frequently not been possible to obtain a uniform coating wall thickness relative to the central axis of the flexible tube. This fact has made it difficult to obtain a homogeneous flexible tube and adversely affects the flexibility of the tube which, of course, should be uniform when the flexible tube is bent during its introduction. In order to alleviate this problem, an arrangement is disclosed in Japanese patent publication No. 1980-17577 in which the basic tubular core structure is first coated with latex through immersion, drying and solidification steps and the like, whereupon a thermoplastic coating is molded onto the latex covered core structure. Although this arrangement avoids the protrusion of the thermoplastic material into the interior of the basic tubular core structure onto the inner surface thereof, it requires complicated manufacturing processes and large-sized molding machines. Accordingly, this arrangement has not been widely adopted.

SUMMARY OF THE INVENTION

Accordingly, it is an object of the present invention to provide new and improved flexible tubes for endoscopes which overcome the disadvantages of conventional flexible tubes as described above.

It is a particular object of the present invention to provide a new and improved flexible tube for an endoscope wherein the formation of wrinkles during introduction of the tube into the body is avoided and which provides uniform flexibility and improved torsional rigidity or rotation-following characteristics whereby the formation of twists in the flexible tube is reduced.

Another object of the present invention is to provide a new and improved flexible tube for an endoscope having improved maneuverability.

Briefly, in accordance with the present invetion, these and other objects are obtained by providing a flexible tube for use in an endoscope comprising a flexible basic tubular core structure including an outer meshwork tube, and a thermoplastic synthetic resin tube bonded to the outer surface of the tubular core structure, i.e., bonded to the meshwork of the meshwork tube, to form a coating layer in a manner such that the resin tube maintains an inherent compressive pre-stress in the finished flexible tube. The compressive pre-stress in the finished flexible tube is accomplished during manufacture by positioning the synthetic resin tube tightly over the basic tubular core structure so that the resin tube exerts a compressive force on the core structure. The synthetic resin tube is heated to a temperature slightly higher than a softening point but lower than a melting point of the thermoplastic resin forming the same whereupon the resin softens and flows into the meshwork of the meshwork tube under the compressive force. The resin tube is then cooled so that the resin hardens bonded to the meshwork tube while retaining an inherent copressive pre-stress in the finished flexible tube. An endoscope tube having flexibility which varies in a step-wise manner from one end of the tube to the other is obtained by integrally bonding two or more thermoplastic synthetic resin tube sections formed of respective resin materials having different hardnesses to the outer surface of the tubular core structure to form a coating la.er in an analogous manner. The ends of adjacent tube sections substantially abut each other and upon heating the tube sections to a temperature higher than a softening point but lower than a melting point of any one of them, the localized regions of the respective pairs of abutting tube section ends are heated to a temperature substantially near a melting point of the tube section having the higher melting point to successively fuse the respective pairs of abutting tube section ends together.

DESCRIPTION OF THE DRAWINGS

A more complete appreciation of the present invention and many of the attendant advantages thereof will be readily understood by reference to the following detailed description when considered in connection with the following non-limiting drawings wherein.

DESCRIPTION OF THE PREFERRED EMBODIMENTS

Figure 1:
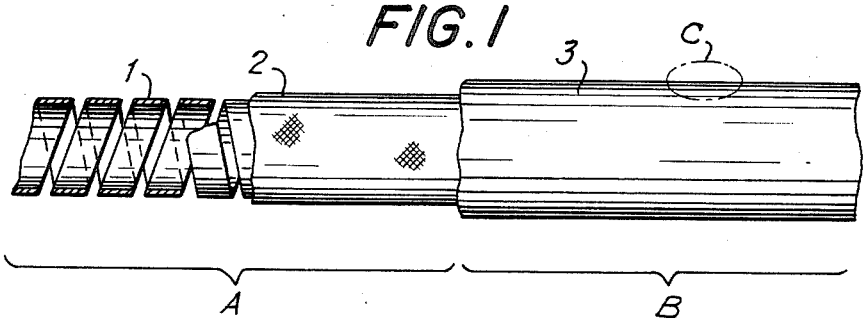
FIG. 1 is a side elevation view, partly in section and partly broken away, of a first embodiment of a flexible tube in accordance with the present invention.
Figure 2:
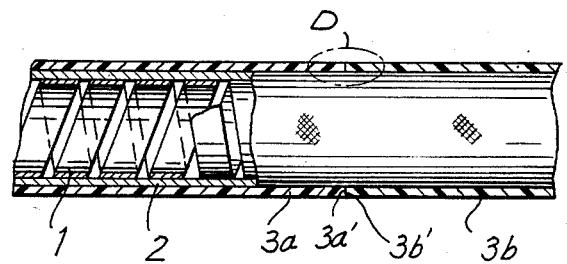
FIG. 2 is a view similar to FIG. 1 illustrating a second embodiment of the flexible tube in accordance with the present invention.

Referring now to the drawings wherein like reference characters designate identical or corresponding parts throughout the several views, and more particularly to FIGS. 1 and 2 thereof, preferred embodiments of a flexible tube in accordance with the present invention are illustrated. Each embodiment comprises a metallic tubular spiral 1 which is resistant to collapsing under external pressure and which is adapted to accommodate and provide protection for various elements and components generally found in endoscopes such, for example, as the optical fiber bundle and a channel receiving means for manipulating forceps and the like. The metallic tubular spiral 1 is provided with a flexibility suitable for its intended use. The metallic tubular spiral 1 is tightly covered around its outer surface with a meshwork tube 2 which functions to restrict longitudinal stretching of the metallic tubular spiral 1. The metallic tubular spiral 1 and meshwork tube 2 constitutes a basic tubular core structure, designated A in FIG. 1, and is substantially similar to prior art core structures of this type.

In accordance with the present invention, the basic tubular core structure A is tightly covered around its outer surface with a thermoplastic synthetic resin tube 3. The tube 3 has an inner diameter which is smaller than the outer diameter of the tubular core structure A and may be formed of material such as polyurethane, soft vinyl chloride, polyethylene or the like. The invention is in part characterized by the manner in which the outer surface of the basic tubular core structure A is tightly covered by the tube 3 and the flexible tube resulting therefrom. More particularly, the thermoplastic synthetic resin tube 3 is homogeneously prepared prior to incorporation in the flexible tube. The synthetic resin tube 3 is positioned tightly over the basic tubular core structure A with a contact pressure therebetween, i.e., so that the resin tube 3 exerts a compressive force on the tubular core structure A, by following a procedure wherein a mandrel having an outer diameter substantially corresponding to an inner diameter of the metallic tubular spiral 1 is inserted into the interior of the metallic tubular spiral 1 so as to temporarily close the hollow interior of the basic core structure, positioning a forcibly enlarged open end of the homogeneous thermoplastic synthetic resin tube 3 over one end of the basic tubular core structure A and supplying or injecting compressed air or other suitable gas into the interior of the thermoplastic synthetic resin tube 3 through its other end. In this manner, the thermoplastic synthetic resin tube 3 is inflated until its inner diameter is sufficiently enlarged to permit the thermoplastic synthetic resin tube 3 to be fed over the meshwork tube 2 of the tubular core structure A.

In a case where the thermoplastic synthetic resin tube 3 has a sufficient flexibility so that its inner diameter can be greatly enlarged under the effect of the injection of compressed air into it, another procedure for tightly positioning the thermoplastic synthetic resin tube 3 over the basic tubular core structure A with a contact pressure therebetween can be employed. In this procedure, the interior of the flexible basic tubular core structure is temporarily closed, such as in the manner described above, whereupon an open end of the thermoplastic synthetic resin tube 3 is releaseably fixed on one end of the basic tubular core structure A, such as by tying or otherwise securing the same thereto. The tube 3 is then inflated by injecting or supplying compressed air into the interior thereof. The thermoplastic synthetic resin tube is then progressively rolled back over and around the basic tubular core structure A from the secured end towards the opposite end thereof so that the outer surface of the meshwork tube 2 is covered around its outer side with the tube 3. Thus, the thermoplastic synthetic resin tube 3 is progressively rolled back from the fixed end thereof to develop the synthetic resin tube axially along the basic tubular core structure such that the original outer surface of the synthetic resin tube is positioned over the outer surface of the basic tubular core structure A.

With the synthetic resin tube 3 positioned over the tubular core structure A by a method described above or the like, the injection of compressed air may be terminated or an amount of compressed air already injected into the tube 3 is exhausted or vented, to position the thermoplastic synthetic resin tube 3 tightly over the basic tubular core structure A on the meshwork tube 2 with a contact pressure therebetween, i.e., with the resin tube 3 exerting a compressive force on the tubular core structure A, resulting from the inherent contractive forces which tend to restore the synthetic resin tube to its unstretched condition.

Figure 6:
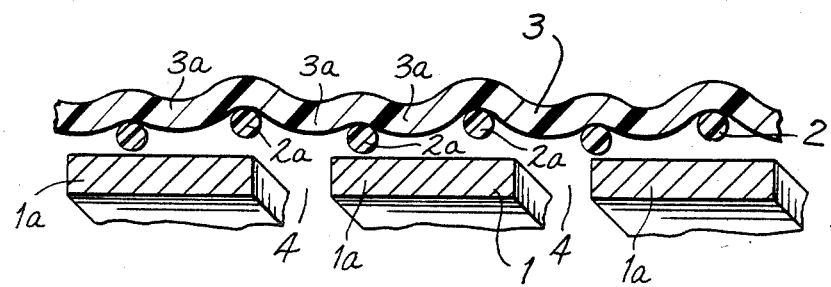
FIG. 6 is an enlarged section view of the area designated "C" in FIG. 1.

The thermoplastic synthetic resin tube 3 tightly positioned over the basic tubular core structure A is then thermally treated by heating the same to temperature slightly higher than the softening point of the synthetic resin forming the tube 3 and lower than the melting point thereof. The tube 3 is thus softened and then allowed to cool whereupon it contracts and enters under its own compressive forces into the fabric mesh of the meshwork tube as seen in FIG. 6. As seen in FIG. 6, portions 3a of resin tube 3 curve at least partially into the spaces between mesh elements 2a. The fact that the resin tube is only softened and not melted results in an inherent compresive pre-stress being retained in the finished flexible tube, i.e., the resin tube now integrally bonded to the meshwork tube of the core structure continues to exert a compressive force on the core structure. The softened resin material will not enter into the gaps 4 (FIG. 6) between adjacent turns 1a of the inner tubular spiral 1 so that the inner surface of the finished flexible tube remains smooth and the outer surface of the resin tube remains even which facilitates insertion of the tube into the body.

The forces of adhesion by which the softened thermoplastic synthetic resin tube 3 is bound to the meshwork tube 2 provided by the resin material entering into the fabric mesh of the meshwork tube and by the inherent compressive pre-stress maintained by the resin tube on the tubular core structure effectively prevents wrinkles from being formed due to compressive forces which occur during introduction of the flexible tube and, moreover, prevents twists from being formed in the flexible tube during rotational manipulation thereof. The flexible tube can be provided if desired with further treatment or working in connection with its finishing.

During the thermal treatment steps described above, an external pressure can be applied to the thermoplastic synthetic resin tube 3 by means of a die or the like while the tube 3 is in its softened state by virtue of the thermal treatment at a temperature higher than the softening point but still lower than the melting point thereof in order to still further improve the bonding of the tube 3 around the meshwork tr:be 2. A portion of the flexible tube completed in accordance with the arrangement described above is designated B in FIG. 1.

Figure 7:
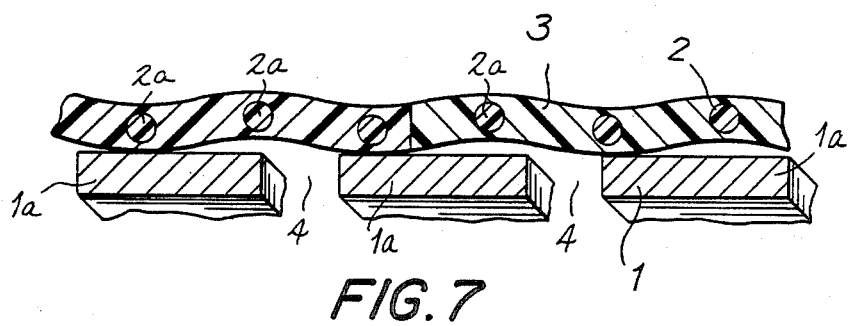
FIG. 7 is an enlarged section view of the area designated "D" in FIG. 2.

Referring now to FIG. 2, another embodiment of the flexible tube in accordance with the present invention is illustrated in which the parts designated by the same reference numerals as in FIG. 1 are similar to those of the embodiment illustrated therein designated by those reference numerals. In the embodiment of FIG. 2, the basic tubular core structure A consists of the metallic tubular spiral 1 and the meshwork tube 2 which externally covers the spiral 1. The outer surface of the meshwork tube 2 is tightly covered with a thermoplastic synthetic resin tube 3 comprising at least two homogeneous thermoplastic synthetic resin tube sections 3a and 3b respectively formed of resin materials having different hardnesses. The synthetic resin tube sections are integrally bonded as a whole to the outer surface of the tubular core structure over the substantial length thereof to form a coating layer in a manner described below. As seen in FIG. 7 and as described below, during the heat treatment the localized regions of the respective pairs of abutting tube section ends 3a' and 3b' are heated to a temperature substantially near the melting point of the tube section have the higher melting point to fuse the pairs of tube section ends together whereupon the mesh elements 2a of the meshwork tube 2 become embedded in the resin material of resin tube 3 without the resin material entering into the gaps 4 between adjacent turns 1a of the inner tubular spiral 1.

A flexible tube for an endoscope may have various constructions depending upon its particular intended use. For example, when it is desired to introduce the front end of a flexible tube which is adapted for permitting observation deep within a particular digestive organ, such as in the case of the diagnosis and/or treatment of the duodenum, the tube must be introduced along a curved path defined by the organ from the mouth. To achieve such introduction in a smooth manner, it is well known that the portion of the tube adjacent to the manipulator unit of the endoscope should have a relatively high rigidity or relatively low flexibility while the portion of the tube adjacent to its front end which is adapted for observation should have a relatively high flexibility, in order to avoid difficulty in the feeding or introduction of the flexible tube in a smooth manner along the curved path of the organ. Thus, if the front end of the endoscope flexible tube which has been adapted to provide a means for observing the organ cannot be smoothly guided along the curve presented by the organ wall within the body cavity during introduction of the flexible tube, the front end may damage the organ wall or, in an extreme case, even rupture the organ wall. Not only are solutions to the problems of injury or rupture to the organ desired but, additionally, an arrangement whereby the flexible tule is prevented from becoming caught on the organ wall and thereby causing the patient pain is also sought.

In view of the practical :anners in which an endoscope is used, such as described above, in the embodiment illustrated in FIG. 2, the flexible tube is provided with a flexibility which varies in a step-wise manner over its length. Referring to FIG. 2, at least two thermoplastic synthetic resin tubes 3a, 3b are provided which are respectively formed of resin material having different hardnesses. The thermoplastic synthetic resin tube sections are successively tightly positioned over the basic tubular core structure with a contact pressure therebetween, i.e., so that each tube section exerts a compressive force on the tubular core structure, and have ends 3a' and 3b' which abut each other. The respective abutting ends 3a' and 3b' of adjacent tube secticns 3a and 3b are adapted so as to be mutually fusible together in a compatible manner. Furthermore, the respective thermoplastic synthetic resin tube sections 3a and 3b are formed of materials which preferably have their melting points as close to each other as possible.

The thermoplastic synthetic resin tube sections 3a and 3b may be tightly positioned on the outer surface of the meshwork tube 2 by any one or a suitable combination of tle two methods described above without any practical difficulty. The thermoplastic synthetic resin tube section 3a and 3b thus positioned on the outer surface of the meshwork tube 2 are softened by heating to a temperature higher than the softening point of the tube section having the highest softening point so that the softened thermoplastic synthetic resin material partially enters into the fabric or tissue mesh of the meshwork tube 2 so that after cooling, the thermoplastic synthetic resin tube sections are integrally bonded to the outer surface of the tubular core structure while retaining an inherent compressive pre-stress in the finished flexible tube. Moreover, during the heat treatment described above, the localized regions of the respective pairs of abutting tube section ends 3a' and 3b' are heated to a temperature which is as close as possible to a melting point of one of the tube sections having a higher melting point than that of the other tube section, whereby the end of the other tube section having a lower melting point is fused with the end of the adjacent tube section, and after cooling of the tube sections, a continuous and integral tube is obtained without any joints or junctures as seen in FIG. 7.

Although the embodiment of FIG. 2 has been described in connection with two thermoplastic synthetic resin tube section 3a and 3b, it will be understood from the foregoing that more than two thermoplastic synthetic resin tube sections of respective different hardnesses may be successively fused together, end to end, so that the resulting flexible tube will have a flexibility which varies in a step-wise fashion over its length. The flexibility increases progressively from the portion of the flexible tube adjacent to the manipulator unit of the endoscope towards the front end thereof which is adapted to provided observation.

Figure 3:
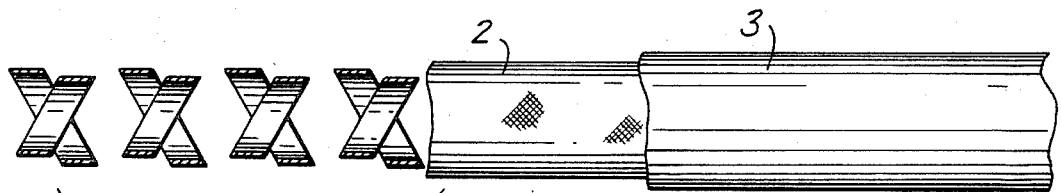
FIG. 3 is a view similar to FIG. 1 illustrating a modification of the embodiment illustrated therein.
Figure 4:
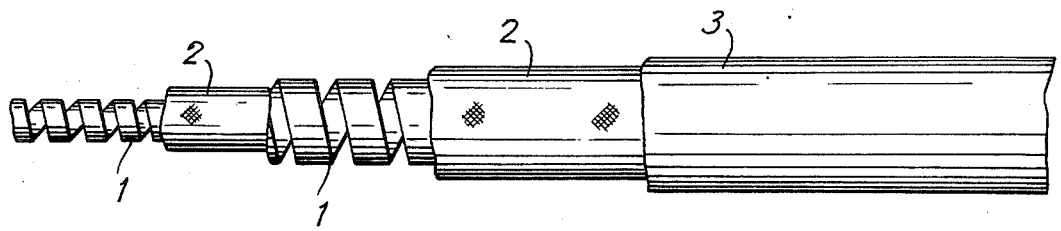
FIG. 4 is a view similar to FIG. 1 illustrating a second modification of the embodiment illustrated therein.

Although the present invention has been described for the sake of simplicity of description with respect to a basic tubular core structure A comprising a single metallic tubular spiral which is covered with a single meshwork tube, it should be understood that the present invention is not limited to such a construction of the basic tubular core structure but may also be applied, without restriction, for example to basic tubular core structure comprising a combination of clockwise and counter-clockwise tubular spirals as seen in FIG. 3 or to basic tubular core structures comprising metallic tubular spirals and meshwork tubes positioned alternately one over the other in a multi-layered manner as seen in FIG. 4.

Figure 5:
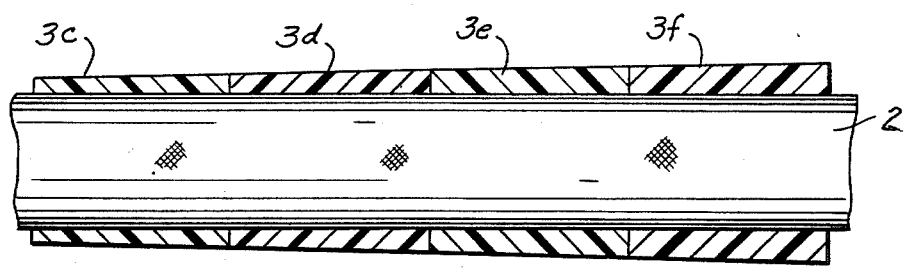
FIG. 5 is a view similar to FIG. 2 and illustrating a modification of the embodiment illustrated therein.

With respect to the embodiment illustrated in FIG. 2, although the flexible tube shown therein incorporates a basic tubular core structure covered by a plurality of thermoplastic synthetic resin tube sections having uniform inner diameters and wall thicknesses, it is understood that the embodiment can be modified as illustrated in FIG. 5 by covering the tubular core structure with a plurality of thermoplastic synthetic resin tube sections 3c, 3d, 3e and 3f, each tube section having a uniform inner diameter and a wall thickness which varies from the thinnest at one end to the thickest at the other end. The plurality of thermoplastic tube sections successively abut one another, end to end, in a manner such that no offset or discontinuity is formed at any juncture or seam. The tube sections are integrally bonded to the core structure by softening and cooling as described above with an inherent compressive pre-stress being retained in the finished flexible tube. The respective pairs of abutting ends of adjacent tube sections are then fused together by heating the localized region of the abutting ends of the adjacent tube sections to a temperature as close as possible to a melting point of one of the tube sections having a higher melting point than that of the other tube section so that the end of the tube section having the lower melting point is fused with the end of the adjacent tube section to obtain a continuous seamless outer surface.

It will be understood from the foregoing description that in accordance with the present invention the flexible tube comprising the basic tubular core structure externally covered with the thermosplastic synthetic resin tube is heated to a temperature higher than the softening point but below the melting point of the synthetic resin tube to thereby tightly bond the synthetic resin tube to the basic tubular core structure while retaining an inherent compressive pre-stress. This construction permits the synthetic resin tube which constitutes a covering for the basic tubular core structure to follow the bending and rotation of the flexible tube without forming wrinkles and twists, respectively. This construction also permits the portions of the flexible tube adjacent to the manipulator unit and to the front end of the flexible tube which is adapted for observation to be maintained in the same orientation so that the flexible tube is sufficiently resistant to compressive forces arising during the introduction of the flexible tube into the body cavity thereby remarkably improving the maneuverability of the flexible tube. Furthermore, problems such as the flexible tube catching on the organ wall within the body cavity are avoided by a flexible tube constructed in accordance with the present invention thereby minimizing any pain caused to the patient. The outer surface of the basic tubular core structure is covered with the homogeneous thermoplastic synthetic resin tube which has been premolded so that the flexible tube obtains a uniform outer coating of the synthetic resin which is integrally bonded around the basic tubular core structure by heat treatment without the protrusion of thermoplastic synthetic resin material into the basic tubular core structure. Thus, a flexible tube for an endoscope which is substantially uniform in all respects is provided by the present invention.

A step-wise or progressive variation of hardness in the flexible tube over its length has conventionally been achieved, for example, by mechanically connecting a plurality of plastic tube pieces of different hardness to the basic core structure. Such mechanical connection inevitably results in discontinuities or offsets and rigid portions at the junctures or seams formed thereby, thereby causing the flexible tube to catch on the inner wall of the body cavity during introduction of the flexible tube preventing a smooth introduction of the tube into the body cavity. In accordance with the present invention, on the contrary, a plurality of thermoplastic synthetic resin tube pieces of respective different hardnesses are successively fused together and integrally bonded to the tubular core structure and, consequently, a flexible tube having a smooth outer surface is provided which can be flexed in conformity with a curved path presented by the organ within the body cavity.

Obviously, numerous modifications and variations of the present invention are possible in the light of the above teachings. It is therefore to be understood that within the scope of the claims appended hereto the invention may be practiced otherwise than as specifically disclosed herein.

What is claimed is:

1. A flexible tube for use in an endoscope, comprising:
   a flexible basic tubular core structure including an inner metallic tubular spiral having a series of turns spaced from each other by gaps and an outer surface constituted by an outer meshwork tube formed of a fabric mesh consituted by mesh elements, said outer meshwork tube being situated tightly over said inner metallic tubular spiral; and
   at least two thermoplastic synthetic resin tube sections, each having a uniform inner diameter and a wall thickness which is thicker at one end of said tube section than at the other end thereof, said tube sections bonded to the meshwork of said meshwork tube, said synthetic resin tube sections having an inner diameter prior to being located over said tubular core structure which is less than an outer diameter of said basic tubular core structure, said bonding being accomplished by,
   (a) expanding the inner diameters of said synthetic resin tube sections and locating the same over said meshwork tube of said tubular core structure with adjacent tube sections abutting at respective ends having substantially the same outer diameter;
   (b) allowing said tube sections to contract so that said tube sections exert a compressive force on said core structure;
   (c) heating said synthetic resin tube sections to a temperature at least slightly higher than a softening point and below a melting point of the synthetic resin of said tube so that the resin softens and enters into the meshwork tube under the compressive force;
   (d) heating only the regions of said abutting ends of said resin tube sections substantially to a melting point of the tube sections to fuse the respective abutting ends to each other;
   (e) cooling said synthetic resin tube sections so that the resin hardens and is integrally bonded to the meshwork of said meshwork tube while retaining an inherent compressive pre-stress in the flexible tube so formed;

said flexible tube so formed having a construction wherein:
(a) said synthetic resin tube sections have at least one of (1) portions which curve at least partially into spaces between said mesh elements of said outer meshwork tube, and (2) regions wherein said mesh elements are embedded therein, so that said resin tube sections are tightly bonded to said meshwork tube;
(b) said resin of said synthetic resin tube sections is totally absent from said gaps between said turns of said metallic tubular spiral; and
(c) said synthetic resin tube sections have an inherent compressive stress acting inwardly on said tubular core structure.

2. A flexible tube for endoscopes as recited in claim 1 wherein said flexible basic tubular core structure comprises a multi-layered structure including a clockwise extending metallic tubular spiral and a counter-clockwise extending metallic tubular spiral.

3. A flexible tube for endoscopes as recited in claim 1 wherein said flexible basic tubular core structure comprises a multi-layer construction including a first inner metallic tubular spiral, a first meshwork tube situtated over said first tubular spiral, a second metallic tubular spiral situated over said first meshwork tube, and a second meshwork tube situated over said second metallic tubular spiral.

* * * * *